United States Patent
Cain

(10) Patent No.: US 11,051,968 B2
(45) Date of Patent: Jul. 6, 2021

(54) VAGINAL URINARY FUNNEL FLASHLIGHT APPARATUS

(71) Applicant: Erik Cain, St. Louis, MO (US)

(72) Inventor: Erik Cain, St. Louis, MO (US)

(*) Notice: Subject to any disclaimer, the term of this patent is extended or adjusted under 35 U.S.C. 154(b) by 238 days.

(21) Appl. No.: 16/441,301

(22) Filed: Jun. 14, 2019

(65) Prior Publication Data

US 2020/0206016 A1 Jul. 2, 2020

Related U.S. Application Data

(60) Provisional application No. 62/787,180, filed on Dec. 31, 2018.

(51) Int. Cl.
| | |
|---|---|
| A61F 5/44 | (2006.01) |
| A61F 5/455 | (2006.01) |
| F21L 4/00 | (2006.01) |
| F21V 23/04 | (2006.01) |
| F21V 33/00 | (2006.01) |
| F21Y 115/10 | (2016.01) |

(52) U.S. Cl.
CPC .......... *A61F 5/4404* (2013.01); *A61F 5/4556* (2013.01); *F21L 4/005* (2013.01); *F21V 23/0421* (2013.01); *F21V 33/0068* (2013.01); *F21Y 2115/10* (2016.08)

(58) Field of Classification Search
CPC ...... A61F 5/4404; A61F 5/4556; F21L 4/005; F21V 23/0421; F21V 33/0068; F21Y 2115/10
See application file for complete search history.

(56) References Cited

U.S. PATENT DOCUMENTS

| | | | |
|---|---|---|---|
| 2,648,335 A * | 8/1953 | Chambers | A61F 5/455 604/347 |
| 5,091,998 A | 3/1992 | Irazabal | |
| 5,893,176 A | 4/1999 | Magiera | |
| 6,758,308 B1 * | 7/2004 | Hearting | B67C 11/02 141/331 |
| 8,490,220 B1 | 7/2013 | Hajek | |
| 2005/0097662 A1 | 5/2005 | Leimkuhler | |
| 2009/0048569 A1 | 2/2009 | Salehi | |
| 2011/0190579 A1 * | 8/2011 | Ziarno | G16H 30/20 600/109 |
| 2014/0082833 A1 * | 3/2014 | Guo | A47K 11/12 4/459 |

FOREIGN PATENT DOCUMENTS

WO WO-2011084018 A2 * 7/2011 ............ A61F 5/451

* cited by examiner

*Primary Examiner* — Rajarshi Chakraborty
*Assistant Examiner* — Glenn D Zimmerman

(57) ABSTRACT

A vaginal urinary funnel flashlight apparatus for allowing easy and accurate illuminated urination includes a funnel body having a cup shaped upper portion and a cylindrical lower portion. The upper portion has a principal opening configured to surround a female genital region. A light sleeve is coupled to the dorsal side of the lower portion. The light sleeve has a proximal end, a distal end adjacent a release aperture of the lower portion, and a light cavity extending through the distal end to proximal the proximal end. A flashlight is slidingly engageable within the light cavity and comprises a flashlight body, a battery, an LED light, and a power switch.

7 Claims, 4 Drawing Sheets

VAGINAL URINARY FUNNEL FLASHLIGHT APPARATUS

CROSS-REFERENCE TO RELATED APPLICATIONS

I hereby claim the benefit under 35 U.S.C. Section 119(e) of U.S. Provisional application 62/787,180 filed Dec. 31, 2018

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to urinary funnels and more particularly pertains to a new urinary funnel for allowing easy and accurate illuminated urination.

BRIEF SUMMARY OF THE INVENTION

An embodiment of the disclosure meets the needs presented above by generally comprising a funnel body having an upper portion and a lower portion. The upper portion is cup shaped and the lower portion is cylindrical. The upper portion has a principal opening configured to surround a female genital region. The funnel body has a dorsal side and a ventral side. A light sleeve is coupled to the dorsal side of the lower portion. The light sleeve has a proximal end, a distal end adjacent a release aperture of the lower portion, and a light cavity extending through the distal end to proximal the proximal end. A flashlight comprises a flashlight body. The flashlight body is slidingly engageable within the light cavity of the light sleeve. A battery is coupled to the flashlight body. An LED light is coupled to the flashlight body and arranged to rest adjacent the distal end when the flashlight body is engaged within the light cavity. The LED light is in operational communication with the battery. A power switch is coupled to the flashlight body and is in operational communication with the battery.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
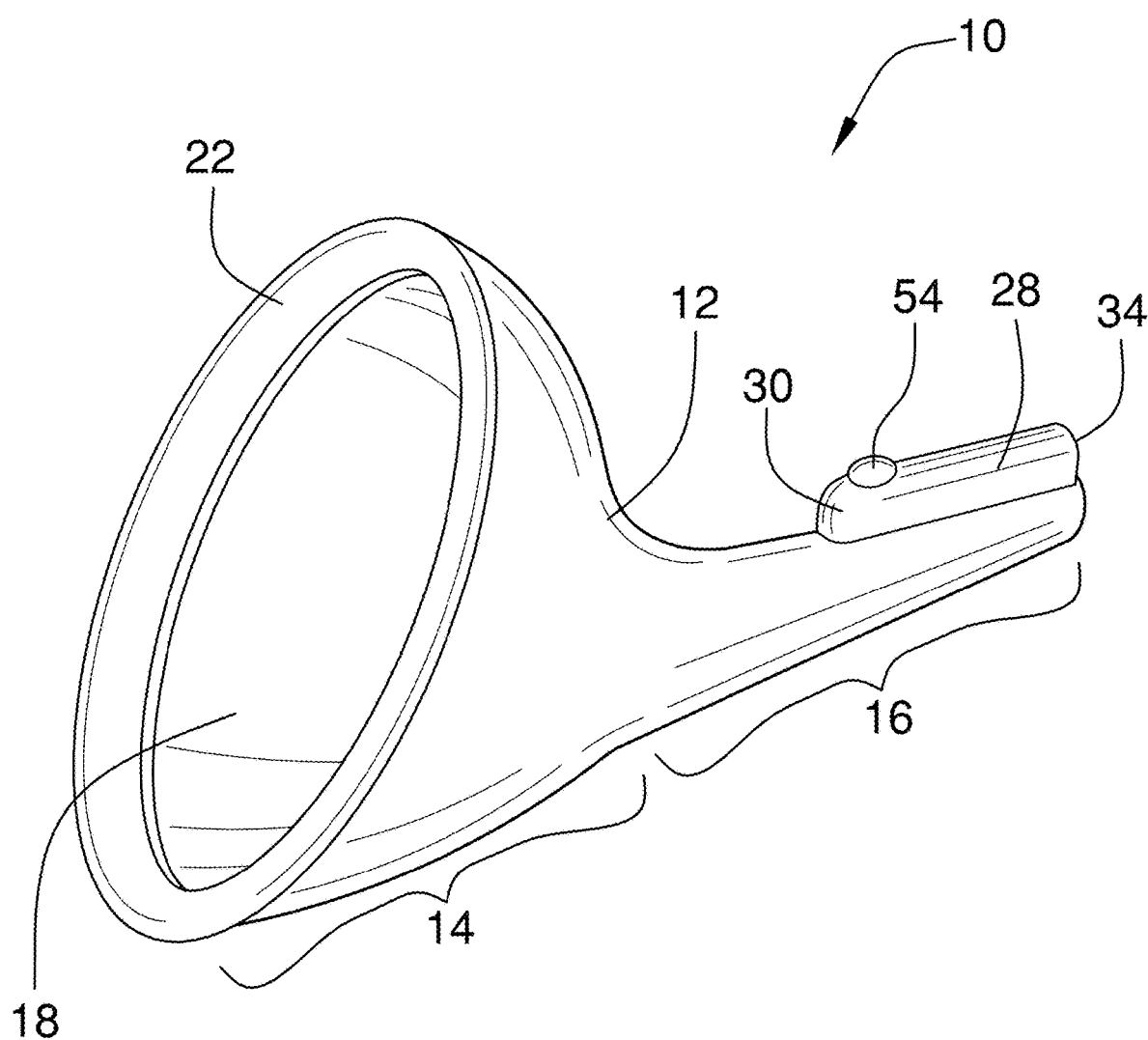
FIG. 1 is an isometric view of a vaginal urinary funnel flashlight apparatus according to an embodiment of the disclosure.
Figure 2:
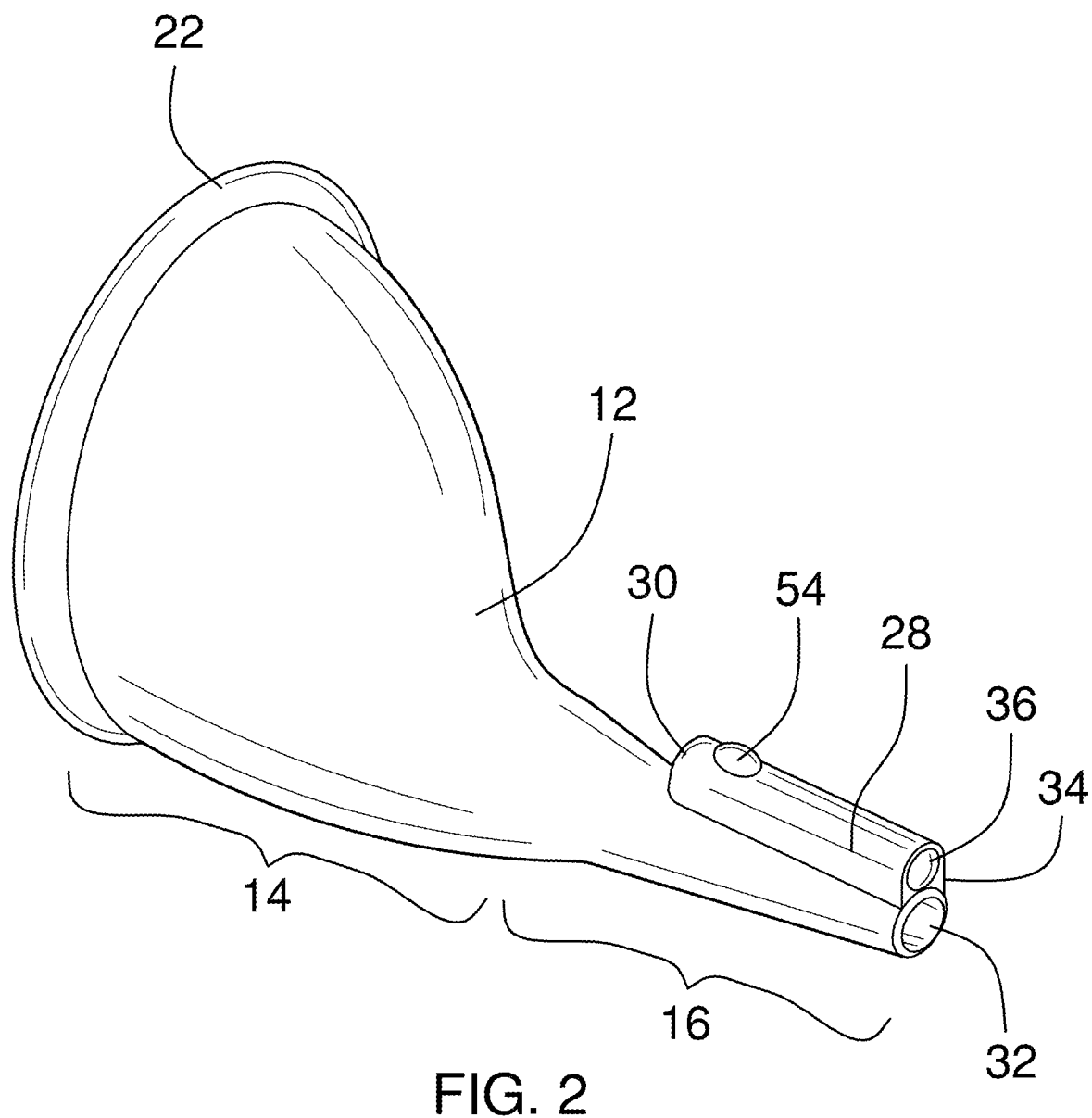
FIG. 2 is an isometric view of an embodiment of the disclosure.
Figure 3:
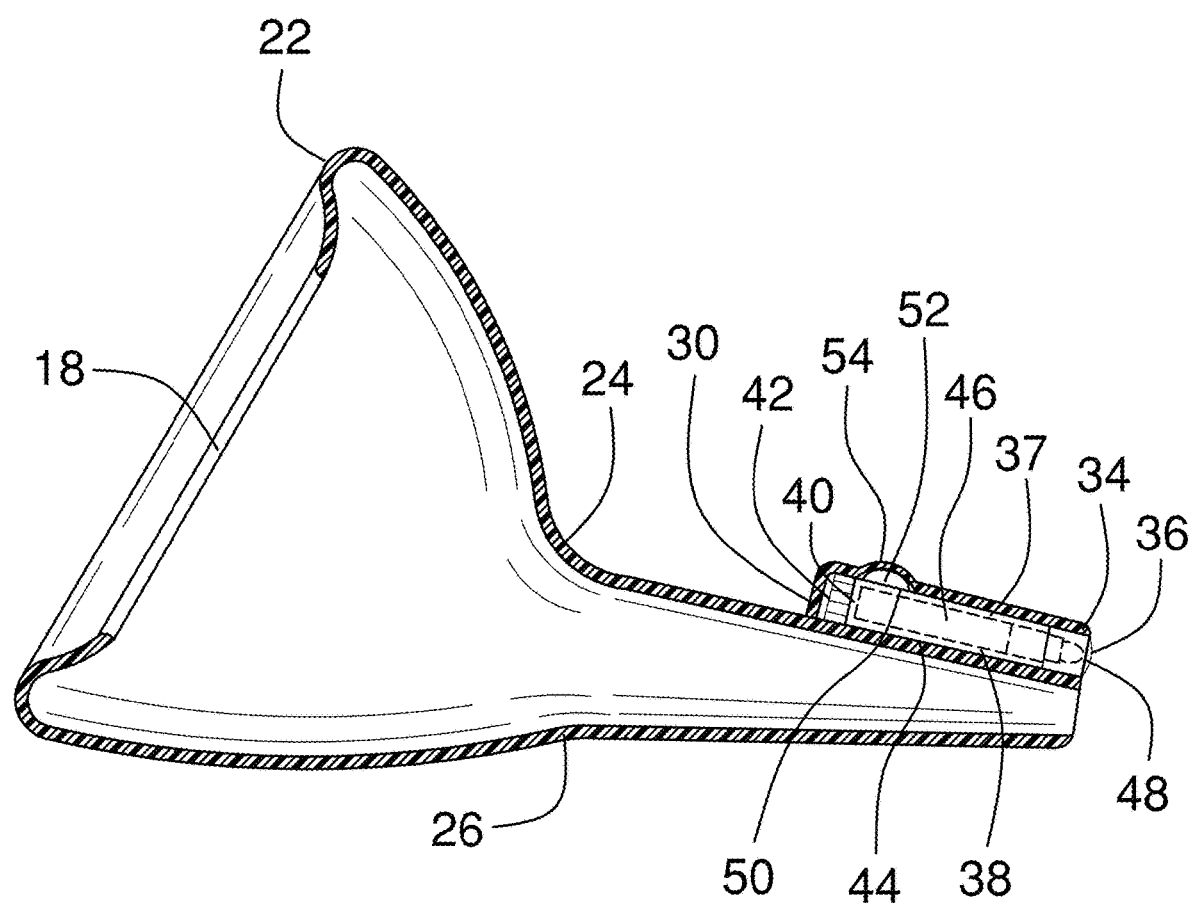
FIG. 3 is a cross-sectional view of an embodiment of the disclosure.
Figure 4:
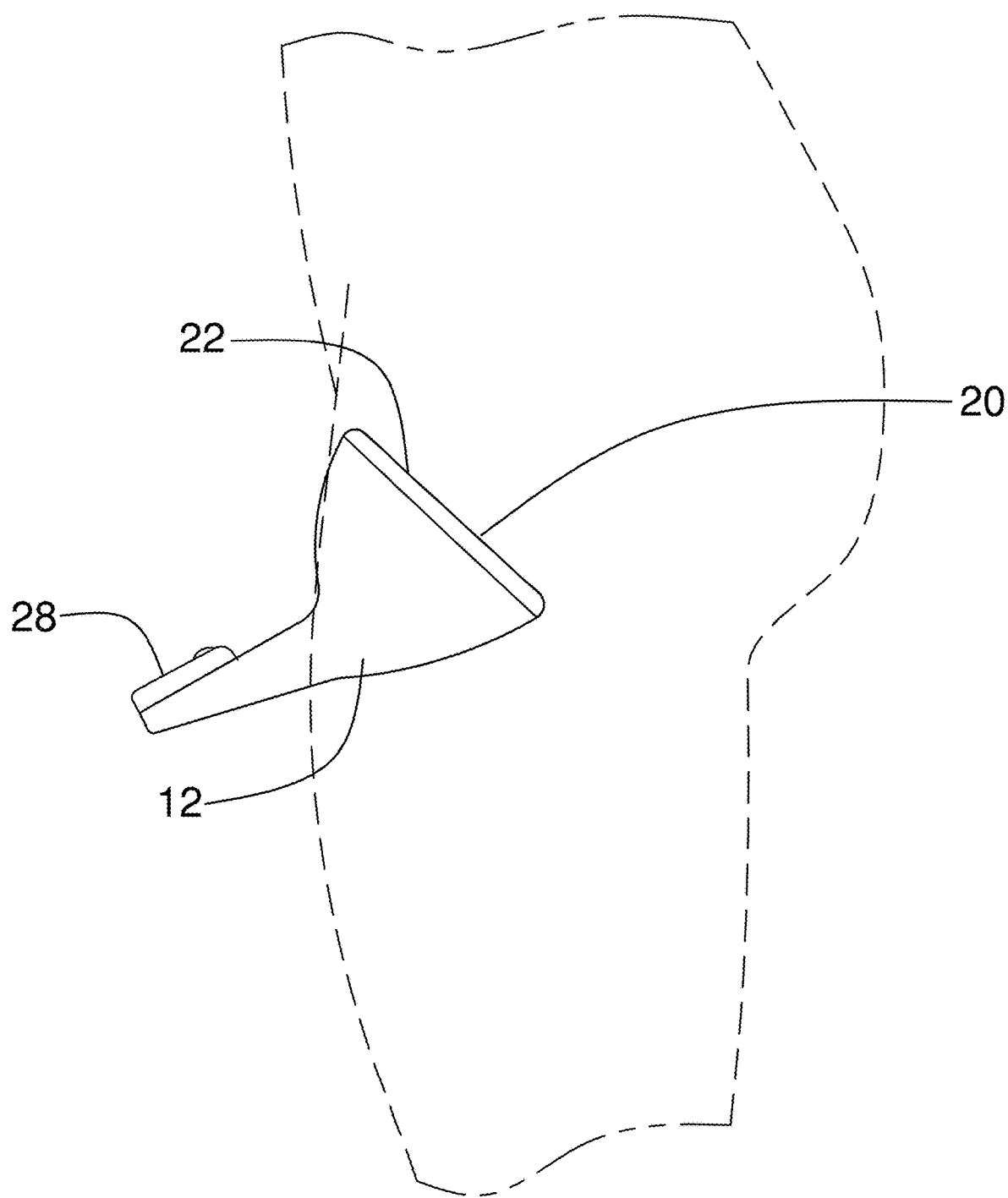
FIG. 4 is an in-use view of an embodiment of the disclosure.

With reference now to the drawings, and in particular to FIGS. 1 through 4 thereof, a new urinary funnel embodying the principles and concepts of an embodiment of the disclosure and generally designated by the reference numeral 10 will be described.

As best illustrated in FIGS. 1 through 4, the vaginal urinary funnel flashlight apparatus 10 generally comprises a funnel body 12 having an upper portion 14 and a lower portion 16. The upper portion 14 is cup shaped and the lower portion 16 is cylindrical and tapered. The upper portion 14 has a principal opening 18 configured to surround a female genital region 20. The upper portion 14 of the funnel body has a rounded lip 22 continuously coupled around a perimeter of the principal opening 18 to create a tight seal against the user's body. The funnel body 12 has a dorsal side 24 and a ventral side 26. The lower portion 16 extends from adjacent the ventral side 26 of the upper portion 14 and is arranged to extend forward from the user's body to best direct urine flow while maintaining a seal with the rounded lip 22.

A light sleeve 28 is coupled to the dorsal side 24 of the lower portion 16 of the funnel body. The light sleeve 28 is coupled to the dorsal side 24 of the lower portion 16. The light sleeve 28 has a proximal end 30 adjacent a release aperture 32 of the lower portion and a distal end 34. The light sleeve 28 has a cylindrical light cavity 36 extending through the distal end 34 to proximal the proximal end 30. The light sleeve 28 has an inverted U-shaped profile and the proximal end 30 is rounded. A flashlight 37 comprises a flashlight body 38. The flashlight body 38 is slidingly engageable within the light cavity 36 of the light sleeve. A back end 40 of the flashlight body 38 has a removable cap 42 to close and alternatively open a battery cavity 44. A battery 46 is coupled within the battery cavity 44. An LED light 48 is coupled to the flashlight body 38 such that the LED light 48 rests adjacent the distal end 34 when the flashlight body 38 is engaged within the light cavity 36. The LED light 48 is in operational communication with the battery 46. A power switch 50 is coupled to the flashlight body 38 and is in operational communication with the battery 46. The power switch 50 may comprise a push button 52 or other type of activation mechanism such as, but not limited to, slider switches, twist knobs, and the like. The light sleeve 28 has a button bubble 54 to receive the push button 52. The push button 52 and the button bubble 54 may be rounded.

In use, the rounded lip 22 is pressed around the user's genitalia while urinating to direct the flow of urine through the release aperture 32. The flashlight 37 is operated with the power switch 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A vaginal urinary funnel flashlight apparatus comprising:
   a funnel body, the funnel body having an upper portion and a lower portion, the upper portion being cup shaped and the lower portion being cylindrical, the upper portion having a principal opening configured to surround a female genital region, the upper portion of the funnel body having a rounded lip continuously coupled around a perimeter of the principal opening, the funnel body having a dorsal side and a ventral side;
   a light sleeve coupled to the funnel body, the light sleeve being coupled to the dorsal side of the lower portion, the light sleeve having a proximal end adjacent a release aperture of the lower portion and a distal end, the light sleeve having a light cavity extending through the distal end to proximal the proximal end, the light sleeve having an inverted U-shaped profile, the proximal end being rounded, the light cavity being cylindrical; and
   a flashlight, the flashlight comprising:
      a flashlight body, the flashlight body being slidingly engageable within the light cavity of the light sleeve;
      a battery coupled to the flashlight body;
      an LED light coupled to the flashlight body, the LED light resting adjacent the distal end when the flashlight body is engaged within the light cavity, the LED light being in operational communication with the battery; and
      a power switch coupled to the flashlight body, the power switch being in operational communication with the battery.

2. The vaginal urinary funnel flashlight apparatus of claim 1 further comprising the lower portion being tapered.

3. The vaginal urinary funnel flashlight apparatus of claim 1 further comprising a back end of the flashlight body having a removable cap, the removable cap closing and alternatively opening a battery cavity, the battery being coupled within the battery cavity.

4. The vaginal urinary funnel flashlight apparatus of claim 1 further comprising the power switch being a push button, the light sleeve having a button bubble to receive the push button.

5. The vaginal urinary funnel flashlight apparatus of claim 1 further comprising the lower portion extending from adjacent the ventral side of the upper portion.

6. The vaginal urinary funnel flashlight apparatus of claim 4 further comprising the push button and the button bubble being rounded.

7. A vaginal urinary funnel flashlight apparatus comprising:
   a funnel body, the funnel body having an upper portion and a lower portion, the upper portion being cup shaped and the lower portion being cylindrical and tapered, the upper portion having a principal opening configured to surround a female genital region, the upper portion of the funnel body having a rounded lip continuously coupled around a perimeter of the principal opening, the funnel body having a dorsal side and a ventral side, the lower portion extending from adjacent the ventral side of the upper portion;
   a light sleeve coupled to the funnel body, the light sleeve being coupled to the dorsal side of the lower portion, the light sleeve having a proximal end adjacent a release aperture of the lower portion and a distal end, the light sleeve having a cylindrical light cavity extending through the distal end to proximal the proximal end, the light sleeve having an inverted U-shaped profile, the proximal end being rounded; and
   a flashlight, the flashlight comprising:
      a flashlight body, the flashlight body being slidingly engageable within the light cavity of the light sleeve, a back end of the flashlight body having a removable cap, the removable cap closing and alternatively opening a battery cavity;
      a battery coupled to the flashlight body, the battery being coupled within the battery cavity;
      an LED light coupled to the flashlight body, the LED light resting adjacent the distal end when the flashlight body is engaged within the light cavity, the LED light being in operational communication with the battery; and
      a power switch coupled to the flashlight body, the power switch being in operational communication with the battery, the power switch being a push button, the light sleeve having a button bubble to receive the push button, the push button and the button bubble being rounded.

* * * * *